United States Patent
Kennington et al.

[11] Patent Number: 5,091,596
[45] Date of Patent: Feb. 25, 1992

[54] METHOD FOR PRODUCING CHIRO-INOSITOL

[75] Inventors: Allison Kennington, Laurel, Md.;
Joseph Larner, Charlottesville, Va.;
Cynthia Hill, Richmond, Va.; Butler
Stringfield, Charlottesville, Va.;
Giorgio Carta, Charlottesville, Va.;
Donald J. Kirwan, Charlottesville,
Va.

[73] Assignee: Univ. of Va. Alumni Patents
Foundation, Charlottesville, Va.

[21] Appl. No.: 631,374

[22] Filed: Dec. 20, 1990

[51] Int. Cl.$^5$ ............................................... C07C 35/16
[52] U.S. Cl. ................................. 568/833; 568/832
[58] Field of Search .............................. 568/833, 832

[56] References Cited

U.S. PATENT DOCUMENTS

| 2,112,553 | 3/1938 | Bartow et al. | 568/833 |
| 2,414,365 | 1/1947 | Elkin et al. | 568/833 |
| 2,456,470 | 12/1948 | Thomas | 568/833 |
| 3,270,064 | 8/1966 | Inaba et al. | 568/833 |
| 3,288,820 | 11/1966 | Argoudelis et al. | 568/833 |

FOREIGN PATENT DOCUMENTS

| 455667 | 4/1949 | Canada | 568/833 |
| 525273 | 5/1956 | Canada | 568/833 |
| 3405663 | 8/1985 | Fed. Rep. of Germany | 568/833 |
| 18476 | 4/1962 | Japan | 568/833 |
| 7327 | 6/1962 | Japan | 568/833 |

OTHER PUBLICATIONS

Mortimer, "Introduction to Chemistry", pp. 347-349 (1977), van Nostrand Comp. New York, N.Y.

*Primary Examiner*—Werren B. Lone
*Attorney, Agent, or Firm*—Whitham & Marhoefer

[57] ABSTRACT

Kasugamycin has been recognized to be a source from which D-chiro-inositol can be easily obtained at low cost and high yield.

10 Claims, 2 Drawing Sheets

D-CHIRO-INOSITOL

D-CHIRO-INOSITOL

KASUGAMYCIN

50g OF KASUGAMYCIN
↓ 2N TRIFLUOROACETIC ACID
3 Hr, 100C
↓ MIXED BED RESIN
FLASH C18 COLUMN
↓
CRUDE D-CHIRO-INOSITOL
↓ RECRYSTALLIZE IN
90% ETHANOL
↓
PURE D-CHIRO-INOSITOL
YIELD: 92% OF THEORETICAL

METHOD FOR PRODUCING CHIRO-INOSITOL

CROSS-REFERENCE TO RELATED APPLICATIONS

The subject invention is related to the following co-pending patent applications which are herein incorporated by reference:

"Dietary Supplement for Insulin-Resistant Diabetics", Larner et al., Serial No. 320482, filed Mar. 8, 1989;

"Screening Method for Diabetic Condition", Larner et al., Serial No. 320485, filed Mar. 8, 1989;

"Purified Insulin Mediators and Purification Process for Same", Larner et al., Ser. No. 320484, filed Mar.8, 1989; and "Quantitative Analysis for Diabetic Condition Predictor", Larner et al., Ser. No. 476953, filed Febr. 8, 1990.

BACKGROUND OF THE INVENTION

1. Field of the Invention

The present invention generally relates to an improved method for producing D-chiro-inositol for the treatment or prevention of insulin-resistant diabetes mellitus, and other related diseases.

2. Description of the Prior Art

As disclosed in the co-pending patent application having Ser. No. 320484, chiroinositol is an essential carbohydrate of the insulin mediator responsible for activating pyruvate dehydrogenase (PDH). In the co-pending patent applications having Ser. Nos. 320485 and 476953, it was shown that lower than normal levels of D- or L-chiro-inositol in samples of a patient's serum or urine is indicative of the patient's predisposition towards diabetes and that extremely low levels of D- or L-chiro-inositol is indicative of a patient suffering from insulin-resistant diabetes. It was suggested, in the co-pending patent application having Ser. No. 320482, that patients suffering from diabetes may in fact be incapable of synthesizing, in vivo, D-chiro-inositol. It was also postulated, as outlined in the co-pending patent application having Ser. No. 320482, that administering a therapeutic dose of D-chiroinositol to patients suffering from diabetes or that are pre-disposed to diabetes can have beneficial affects.

The methyl ester of D-chiro-inositol, D-chiro (+)-o-methyl inositol (also known as pinitol), has been isolated from the leaves of the Bougainvillea spectabilis (BVS) plant. This procedure requires repeated extractions with alcohol and water followed by drying the alcoholic extract and then extracting the dried alcoholic extract successively by hot-percolation with petroleum ether, benzene, ethyl acetate, and methanol. Pinitol is eluted as a crystalline compound having a melting point (M.P.) of 190° C. The yield of pinitol after this procedure of several successive extractions is only 10%. Moreover, pinitol must then be de-esterified using hydroiodic acid (HI) to produce D-chiroinositol.

Arthur B. Anderson has disclosed methods for extracting pinitol from sugar pine (Pinus lambertina Douglas) in *Industrial and Engineering Chemistry*, Vol. 45, March 1953, pp. 593–96, and in *TAPPI*, Vol. 35, No. 5, May 1952. Schweizer et al. has disclosed that various esterified forms of chiro-inositol can be isolated from chick peas and other legumes in *J. Sci. Food Agric.*, Vol. 29, pp. 148–54 (1978). The isolation techniques disclosed in Anderson and Schweizer et al. are also tedious, time consuming endeavors which require multiple extractions and produce relatively low yields, and they are analogous to the isolation technique discussed above in connection with the isolation of pinitol from BVS. Likewise, the isolated product obtained from the Anderson and Schweizer et al. processes must be de-esterified to produce chiroinositol D-chiro-inositol can also be produced by the direct inversion of the three position hydroxy constituent of myo-inositol using the organic synthetic methodology described by Shen et al. in *Tetrahedron Letters*, Vol. 131, No. 8, pp. 1105–8 and 1109–12, 1990. Myo-inositol is not a particularly good source of D-chiro-inositol because the present synthetic methodology is very expensive.

Kasugamycin is an antibiotic compound having a chemical formula of $C_{14}H_{25}O_9N_3$. Kasugamycin was discovered in the mid-1960s and is discussed in U.S. Pat. No. 3,358,001 to Umezawa et al. As disclosed in U.S. Pat. No. 3,607,657, to Umezawa et al., Kasugamycin can be produced by cultivating a strain of streptomyces named Streptomyces kasugaspinus. Kasugamycin is a white amorphous powder which has no definite melting point. It has been shown to be useful in medicine as a therapeutic in the treatment of Pseudomonas infections in humans and is also useful in the prevention of rice blast disease. Since kasugamycin has a very low toxicity to humans, it is ideally suited for use as an agricultural chemical. Other U.S. Patents which generally relate to kasugamycin and its use are the following: U.S. Pat. Nos. 3,681,398 to Umezawa et al, 3,856,969 to Umezawa et al., and 3,968,100 to Umezawa.

SUMMARY OF THE INVENTION

It is therefore an object of the present invention to provide an inexpensive, less time consuming method for producing D-chiro-inositol.

It is another object of the present invention to use kasugamycin as a source of D-chiro-inositol.

According to the invention, the inventors have recognized that administering therapeutic amounts of D-chiro-inositol to patients suffering from or that are pre-disposed to diabetes can have beneficial affects and that a need exists for a low cost, less time consuming method for producing D-chiro-inositol. In particular, the inventors have found that D-chiro-inositol can be produced quickly and in high yield using kasugamycin as a starting material. Before the invention by the inventors, D-chiro-inositol had been produced by the extremely time consuming extraction techniques discussed above or by the direct inversion of myo-inositol. It was the inventors discovery that kasugamycin, which was a known antibiotic compound, had a chemical structure that would allow for easy production of D-chiro-inositol simply by breaking apart the kasugamycin molecule.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figures 1, 2, 3:
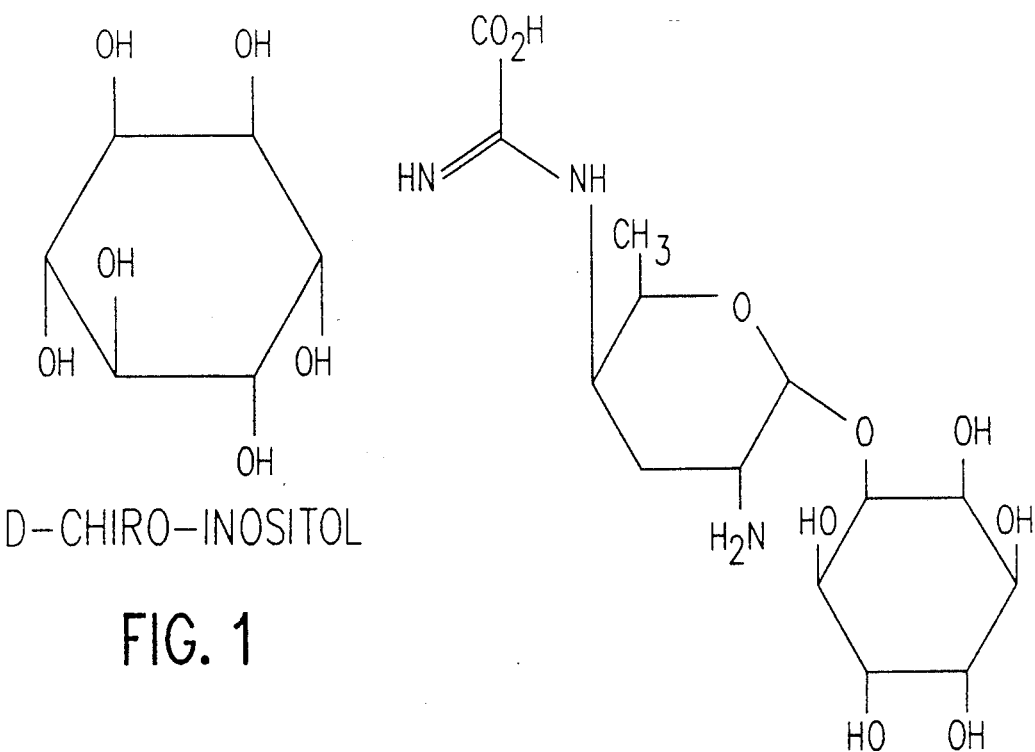
FIG. 1 is structural drawing of D-chiroinositol.
FIG. 2 is a structural drawing of kasugamycin.
FIG. 3 is a flow diagram showing one method of producing D-chiro-inositol from kasugamycin.

Referring now to the drawings, and more particularly to FIG. 1, there is shown the structural formula for D-chiro-inositol. D-chiroinositol can be chemically synthesized by any number of organic synthetic pathways. However, the yield from attempting to chemically synthesize D-chiro-inositol would be extremely low because geometrically organizing the bonded hydroxyl constituents correctly in space is not a straightforward procedure. Therefore, efforts have been made to find the compound in nature. As has been discussed above, D-chiro-inositol can be isolated from pine needles or chick peas via a long, tedious process of extraction, elution, and de-esterification. While the yield from these isolation procedures is only approximately 10%, these methods are still far superior to chemical synthetic methods which would start with benzene, for example.

The inventors have discovered that D-chiroinositol can be easily produced from kasugamycin, which is a known antifungal, aminoglycoside antibiotic compound naturally produced by a variety of bacteria. FIG. 2 shows the chemical structure of kasugamycin. The important feature noted by the inventors is that D-chiro-inositol is one of the two carbohydrate units in kasugamycin. In essence, by breaking the bond between the two carbohydrate units, the applicants could obtain D-chiro-inositol in high yield at low cost. The inventors recognition that kasugamycin can be used as a source of D-chiro-inositol is new and the simple separation technique for separating the two sugar molecules of kasugamycin is also new. Using kasugamycin as a source of D-chiro-inositol results in savings in labor and other costs.

FIG. 3 shows that purification of D-chiroinositol from kasugamycin is relatively simple. D-chiro-inositol can be produced at a laboratory scale according to the following procedure. First, 50 grams (g) of kasugamycin.HCl is hydrolyzed with 500 milliliters (ml) of 2 normal (N) trifluoroacetic acid to yield a cloudy white solution. Kasugamycin.HCl is the hydrochloride salt of kasugamycin and is available from the Sigma Chemical Company of St. Louis. The cloudy white solution is then heated at 80°-100° C. for three hours. After cooling, the solution is passed through a mixed bed of ion exchange resins to remove ionic compounds. In particular, the solution is first passed through 450 g of Amberlite IRA 400+ which is a strongly acidic resin, and then the solution is passed through 450 g of Amberlite IR120 which is a strongly basic resin. The two resins are available from the Sigma Chemical Company of St. Louis.

After passing the solution through the mixed bed of resins, the mixed bed of resins is washed with 200 ml of water and the water that passes through the mixed bed is added to the kasugamycin hydrolysis material. The combined solutions are then filtered through a bed of C18 flash chromatography gel, available from the J. T. Baker Company. The C18 flash chromatography gel removes hydrophobic material from solution. The filtered material is then reduced to dryness by rotavapping, filtering, or any other suitable technique, to produce off-white crystals. Minimal heat, e.g., less than 40° C., should be used while removing the solvent. Recrystallization from 90% ethanol produces approximately 20 g of pure D-chiroinositol (a yield of approximately 80%).

D-chiro-inositol produced as described above was tested using classical nuclear magnetic resonance (NMR) and gas chromatography (GC) techniques. The NMR spectra showed highly defined proton-proton splitting. The GC chromatogram showed only one major peak which was for D-chiroinositol. No traces of the other carbohydrate unit from the kasugamycin were detected. The D-chiroinositol produced as described above was 99% (+) pure. The applicants point out that scale up for production quantities should be easily accomplished.

Figure 4:
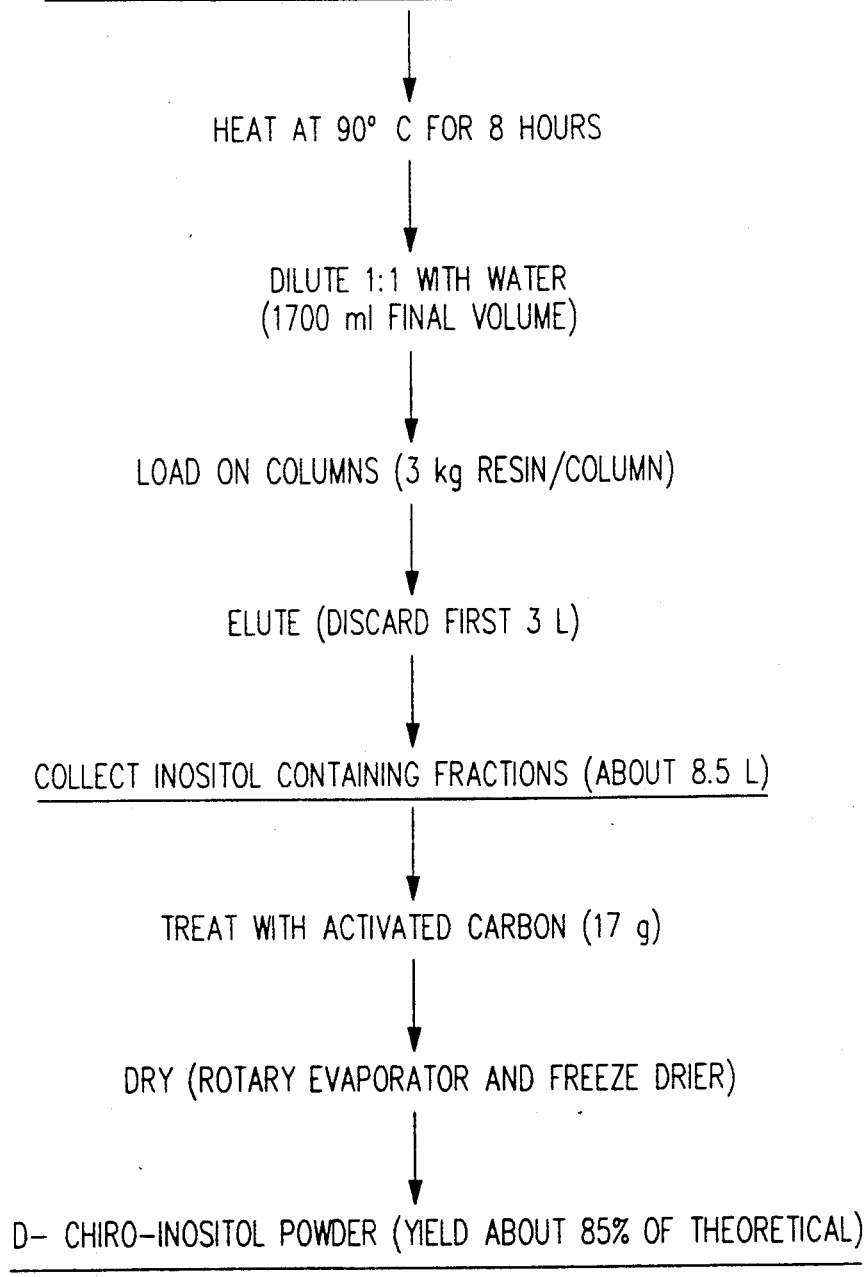
FIG. 4 is a flow diagram showing another method of producing D-chiro-inositol from kasugamycin.

FIG. 4 shows an alternative method for producing D-chiro-inositol from kasugamycin.

The first two process steps are directed to the hydrolysis of kasugamycin with hydrochloric acid. First, a 30% weight per volume (w/v) solution of kasugamycin hydrochloride in 5 N HCl is produced, e.g., 225 grams of kasugamycin + 700 ml of 5 N HCl, and the solution is heated and stirred to yield a clear solution. Second, the solution is heated for eight hours at 90° C. using a forced air oven or the like. The solution does not need to be agitated while it is heated for the eight hours. After the eight hours has expired, the solution will be brown in color.

The next four process steps are directed to the preparative chromatography and collection of hydrolysis products. An anion exchange column, such as the Amberlite IRA 410, hydroxide form, is connected in series with a cation exchange column, such as the Amberlite IR120+, hydrogen form. About 13 grams of each resin is required for each gram of kasugamycin in the hydrolysis solution; hence, for the 225 g of kasugamycin example, approximately 3 kilograms of resin per column will be required. Prior to chromatography, the brown colored solution obtained by the hydrolysis and heating steps described above is diluted 1:1 with water. Then the solution is loaded onto the columns at room temperature at a rate of 1 cm/min. Elution with water occurs at 1 cm/min at room temperature with the first three liters being discarded. All fractions containing D-chiro-inositol are collected and pooled. In the present example, approximately 8.5 liters of eluate containing D-chiro-inositol are collected. The eluate can be clear or colored. The pH of the eluate should be neutral. After collection and pooling, the eluate is refrigerated for storage.

The next process step is directed toward treating the eluate with activated carbon, and this particular example, preferably 17 grams of activated carbon are used. Treating the eluate with activated carbon gets rid of certain impurities and yields a colorless solution. In the present example, 2 grams per liter of activated carbon is added to the eluate and the mixture is stirred for two hours at 5° C. The mixture is then filtered to remove the carbon and to render a colorless solution.

The next two process steps are directed toward drying the colorless solution/eluate to obtain D-chiro-inositol and crushing the D-chiro-inositol into a powder. Preferably, the eluate is first reduced to ten percent using rotary evaporation at 35° C. Then the solution is transferred to trays for freezing. The D-chiro-inositol will crystallize on cooling. After freezing, the D-chiro-inositol is dried by lyophilization using an ambient temperature of not more than 35° C. The product should be a white cake which is easily crushed to yield a white powder.

Using the method shown in FIG. 4, an experimental yield of 85% of the theoretical yield was obtained. The product was analyzed using HPLC with a BioRad HPX-87H column with a 0.01 N sulfuric acid eluent at a flow of 1.0 ml/min and a 60° C. temperature for the column and the detector. A Waters refractive index detector was used and a Hewlett Packard 3392A integrator using peak area was used for data acquisition.

While the invention has been described in terms of its preferred embodiment where laboratory quantities of kasugamycin have been used to produce a pure D-chiro-inositol, those skilled in the art will recognize that the invention can be practiced with modification within the spirit and scope of the appended claims.

Having thus described the invention, what we claims as new and desire to secure by Letters Patent is as follows:

1. A method of producing D-chiro-inositol from kasugamycin, comprising the steps of:
   providing a quantity of kasugamycin;
   hydrolyzing said quantity of kasugamycin with a hydrolyzing agent under suitable time and temperature conditions so as to obtain an aqueous mixture of D-chiro-inositol and reaction products from said quantity of kasugamycin;
   passing said aqueous mixture of D-chiro-inositol and reaction products through a cation exchange medium capable of binding anionic reaction products and impurities in said aqueous mixture and an anion exchange medium capable of binding cationic reaction products and impurities;
   removing other impurities from an eluate from said cation and anion exchange medium; and
   obtaining D-chiro-inositol from said eluate.

2. A method as recited in claim 1 wherein said step of obtaining D-chiro-inositol is performed by partial drying of said eluate and then freeze drying a remaining fraction.

3. A method as recited in claim 1 wherein said step of obtaining said D-chiro-inositol is performed by completely drying said eluate to obtain dried D-chiro inositol.

4. A method as recited in claim 3 further comprising the step of purifying said dried D-chiro-inositol.

5. A method as recited in claim 4 wherein said step of purifying includes recrystallization.

6. A method as recited in claim 1 wherein said step of hydrolyzing is performed with an acidic hydrolyzing reagent.

7. A method as recited in claim 6 wherein said temperature conditions range from 80° C. to 100° C.

8. A method as recited in claim 6 wherein said time conditions range from three to eight hours.

9. A method as recited in claim 1 wherein said step of removing other impurities is performed using activated carbon.

10. A method as recited in claim 1 wherein said step of removing other impurities is performed using C18 flash chromatography gel.

* * * * *